US011844357B2

(12) United States Patent
Eger

(10) Patent No.: US 11,844,357 B2
(45) Date of Patent: Dec. 19, 2023

(54) OPTICALLY ASSESSING BODY PROPERTIES

(71) Applicant: Horst Eger, Ahrensfelde (DE)

(72) Inventor: Horst Eger, Ahrensfelde (DE)

(*) Notice: Subject to any disclaimer, the term of this patent is extended or adjusted under 35 U.S.C. 154(b) by 215 days.

(21) Appl. No.: 16/956,274

(22) PCT Filed: Dec. 19, 2017

(86) PCT No.: PCT/DE2017/101085
§ 371 (c)(1),
(2) Date: Jun. 19, 2020

(87) PCT Pub. No.: WO2019/120342
PCT Pub. Date: Jun. 27, 2019

(65) Prior Publication Data
US 2020/0315192 A1   Oct. 8, 2020

(51) Int. Cl.
*G06K 9/00* (2022.01)
*A22C 17/00* (2006.01)
(Continued)

(52) U.S. Cl.
CPC ........ *A22C 17/0073* (2013.01); *A22C 15/008* (2013.01); *A22C 17/0006* (2013.01);
(Continued)

(58) Field of Classification Search
CPC ...................................................... A22B 5/007
See application file for complete search history.

(56) References Cited

U.S. PATENT DOCUMENTS 6,563,580 B1 * 5/2003 Aignel ................. G01N 33/12
250/910
9,675,091 B1    6/2017 Eger
(Continued)

FOREIGN PATENT DOCUMENTS

DE    102005010183 A1   9/2006
GB       2239787 A       7/1991
(Continued)

OTHER PUBLICATIONS

International Preliminary Examination Report dated Jul. 2, 2020, from PCT Application No. PCT/DE2017/101085, of which the present application is a 371 national entry.
(Continued)

*Primary Examiner* — Hadi Akhavannik
(74) *Attorney, Agent, or Firm* — KRIEGSMAN & KRIEGSMAN

(57) ABSTRACT

Method and system for optically assessing properties of a body on at least one sectional surface of at least one cut introduced in the body in question. The sectional surface is thereby optically recorded directly during the cutting operation by an image acquisition unit, namely, by means of optical sensors of a blade of a cutting tool that is designed for this purpose. The data resulting from a digitization of the sensor signals that have been converted into electrical signals are then processed in an image processing device to visualize the at least one sectional surface on at least one display or/and to create reports in regard to the characteristics of the body or/and in order to classify the body in accordance with a classification system, or/and to derive control signals for a subsequent further processing of the body or of parts produced by the execution of the at least one cut.

16 Claims, 3 Drawing Sheets

Figure 1:
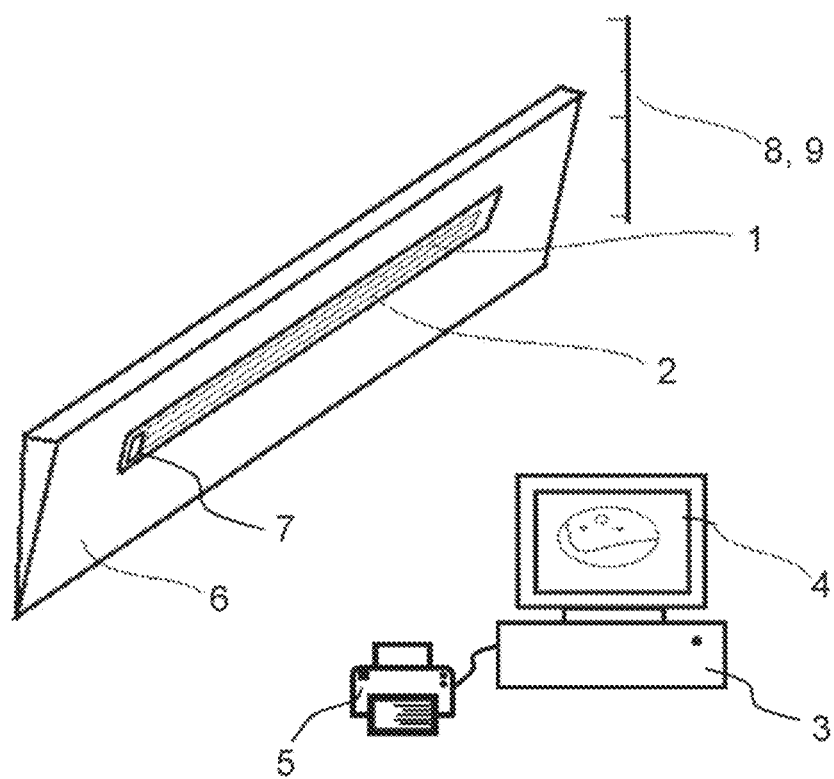

(51) Int. Cl.
  *G06T 7/62* (2017.01)
  *G06T 7/70* (2017.01)
  *G01N 33/12* (2006.01)
  *G06T 7/00* (2017.01)
  *H04N 5/38* (2006.01)
  *A22C 15/00* (2006.01)
  *G06F 18/24* (2023.01)
  *H04N 23/54* (2023.01)
  *H04N 23/56* (2023.01)

(52) U.S. Cl.
  CPC ...... *A22C 17/0033* (2013.01); *A22C 17/0086* (2013.01); *G01N 33/12* (2013.01); *G06F 18/24* (2023.01); *G06T 7/0004* (2013.01); *G06T 7/62* (2017.01); *G06T 7/70* (2017.01); *H04N 5/38* (2013.01); *H04N 23/54* (2023.01); *H04N 23/56* (2023.01); *G06T 2207/30128* (2013.01)

(56) References Cited

U.S. PATENT DOCUMENTS

| | | | |
|---|---|---|---|
| 2003/0072472 | A1 | 4/2003 | Haagensen et al. |
| 2004/0153283 | A1* | 8/2004 | Wargon ............... G01B 21/00 702/156 |
| 2005/0085176 | A1 | 4/2005 | Houtz |
| 2007/0275647 | A1 | 11/2007 | Eger |
| 2014/0005484 | A1* | 1/2014 | Charles ............... A61B 34/20 600/201 |
| 2016/0343120 | A1* | 11/2016 | Johnson ............... G06T 7/0008 |
| 2020/0074613 | A1 | 3/2020 | Eger |

FOREIGN PATENT DOCUMENTS

| | | |
|---|---|---|
| WO | 02060656 A1 | 8/2002 |
| WO | 2007022782 A2 | 3/2007 |

OTHER PUBLICATIONS

"Vermarktung von Schlachttieren," Hochschule Anhalt University of Applied Sciences, Sachsen-Anhalt, Germany, www.kolleg.loel.hs-anhalt.de/cmsloel/326.html (2013).

* cited by examiner

OPTICALLY ASSESSING BODY PROPERTIES

The invention relates to a solution for optically assessing properties of a body on the basis of an invasive intervention in the body in question. It relates, in particular, to a method in which the assessment of the body properties is produced on at least one sectional surface of at least one cut introduced in this body. Beyond this, the subject of the invention is a system that is suitable for carrying out this method. A preferred field of application of the invention is represented by the invasive assessment of the characteristics of the meat on a body or carcass of a slaughtered animal or on the parts thereof in an optical way, albeit without any limitation of the invention thereto.

In principle, the body that is to be assessed by use of the invention can be a body of any kind. Thus, it can involve a dead body, that is, a lifeless body, as well as a living body, whereby the former need not only be merely a physical or geometric body, that is, an object or part of an object in the usual sense, but rather what is involved can also be the body of an originally living organism or parts thereof with respect to the already mentioned carcass of a slaughtered animal or parts thereof. In regard to the preferred intended use of the invention and the relevant prior art that is known here, however, the following explanations are made, above all, with reference to an (invasive) optical assessment of the carcasses of slaughtered animals, without—as already stated—thereby indicating any limitations of the invention in this regard.

In connection with the industrial processing of meat and the production of meat products, it is usual to assess the quality of the meat at the earliest possible phase of meat processing so as, on the basis of such an assessment, either to establish in a fundamental manner in what way or to which products the parts of a carcass of a slaughtered animal are to be processed, or however, within an existing classification system, to assign independently treated parts of the carcass of a slaughtered animal to a specific quality class or marketing class. The optical assessment of the meat plays an important role here. In terms of corresponding classifications and the procedure for assignment of the individual parts of a carcass of a slaughtered animal to a respective specific class as well as in terms of the quality assessment of meat in general, there exist very different regulations in individual countries. This is also true for the optical assessment.

For the purpose of an assessment of the meat characteristics of the carcasses of slaughtered pork, for example, the use of so-called Fat-O-Meaters is known. What is involved here are pistol-shaped handheld instruments having a pointed tip probe that is driven into the carcass of the slaughtered animal when the instrument is appropriately actuated. The probe behind the tip, which usually has an essentially circular cross section with a diameter of 6 mm to 8 mm, is equipped with optical sensors. In interaction with a processing device that analyzes the signals of the optical sensors, these probes are used, in particular, to determine the thickness of the muscle tissue of a pork cutlet, for example.

The basic structure of a probe of the aforementioned kind is described, for example, at www.kolleg.loel.hs-anhalt.de/cmsloel/326.html in "Vermarktung von Schlachttieren" (Marketing of Slaughtered Animals). By use of such a probe, it is possible to record data in regard to the meat characteristics of a carcass of a slaughtered animal in a single measuring operation, albeit only very locally and in a manner that is focused on a limited region. Hence, for example, it is hardly possible to make statements in regard to the marbling of a cutlet or—in the case of beef—in regard to the marbling of the rib eye.

A larger area assessment and, in particular, also statements in regard to the marbling of the meat are possible, in contrast, by means of the image analysis system described in US 2003/0072472 A1. A component of this system is likewise an optical measuring or sensor head that is guided by hand. The wedge-shaped sensor head is specially designed here for optically recording the tissue at the sectional surface of a cut that is introduced in the region of the rib eye in a carcass of slaughtered beef. An assessment of the meat of a carcass of slaughtered beef on the basis of a cut introduced in this way is usually carried out predominantly in the USA and in Canada. In this case, it has proven advantageous when the sectional surfaces resulting from a cut introduced in the aforementioned region in a beef carcass are routinely spaced relatively far apart. In this way, it is possible for the wedge-shaped sensor head described in the specification to be inserted readily into the cut introduced in the carcass.

However, in connection with meat assessment in the case of beef carcasses, it is usual—for example, in Europe and in South America—to make a cut in a different manner. In this case, for example, a cut is introduced in the beef carcass in the region between the 5th rib and the 7th rib or, for instance in Germany, in the region between the 10th rib and the 11th rib. When the cut is introduced in this manner, however, the sectional surfaces are usually spaced less far apart than in the case of a cut introduced in the region of the rib eye. The use of the sensor head described in US 2003/0072472 A1 is thus possible only with limitation or, in any case, is at least markedly more difficult to perform.

The object of the invention is to provide an alternative solution to the invasive optical assessment of the properties of bodies that, in particular, is also suitable for the assessment of the characteristics of the meat on the carcasses of slaughtered animals. In regard to the latter, that is, to an assessment of meat characteristics, the corresponding solution is intended to make possible thereby the assessment above all on pork and on the carcasses of slaughtered beef and thereby to be employable regardless of the different regulations existing on individual continents or in individual countries. For this purpose, a method and a system that is suitable for carrying out this method are presented.

The object is achieved by way of a method having the features of the patent claim 1. A system that achieves the object is characterized by the first independent device claim. Advantageous elaborations or further developments of the invention are given by the respective dependent claims.

In accordance with the object, what is involved in the method according to the invention for optically assessing bodies is an invasive method, namely a method in which the respective body is not assessed optically in a purely external manner, but rather in which sensing elements are introduced into the body in question. In accordance with the method proposed for the solution of the problem, at least one sectional surface of at least one cut that is introduced in the body that is to be assessed (if need be, also extending all the way through this body) is recorded optically by means of corresponding sensors of an image acquisition unit. The data resulting from a digitization of the sensor signals that have been converted to electrical signals are processed in an image processing device, namely, for visualization of the at least one sectional surface on at least one display or/and for creation of a report describing the characteristics of the body along the at least one sectional surface or/and for classification of the body in accordance with a classification system or/and for derivation of control signals for a subsequent further processing of the body or of the parts that are created from it when the at least one cut is executed.

In accordance with the invention, the optical recording of the at least one sectional surface occurs already directly during the cutting operation by way of a blade of a cutting tool that is designed for this purpose. The analog electrical sensor signals that, during scanning of the (the at least one) sectional surface in question, result from the conversion of the optical signals impinging on the optically active areas of the sensor are digitized and thereby coded via digital data for further processing. In a hardware- and software-based image processing device, the digital data that are created are finally processed, as already discussed above, for the purpose of visualizing the at least one sectional surface on at least one display, for the creation of reports, for the classification of the body, or/and for the derivation of control signals for other processing devices. Through application of the method and by means of the system that is yet to be explained, it is accordingly possible to cut a carcass of a slaughtered animal or a part thereof, such as, for example, a complete pork loin or a complete roast beef, or also sausage, smoked ham, cheese, baked goods, wood, or other body, slice by slice by using one blade or a plurality of blades to produce slices and, at the same time, to investigate them thereby in terms of dimensions, quality, or other characteristics.

In the following discussions and in the patent claims, a distinction in terms is made between (optical and electrical) signals on the one hand and electrical data on the other hand. In accordance with the understanding that underlies this distinction, signals involve analog variables, namely, for example, optical signals detected in the form of brightness or/and color by the sensors during scanning of the sectional surface and electrical signals created from these optical signals by converting them in the sensors. Electrical data, in contrast, represent in digital form the aforementioned electrical signals resulting from the optical signals, so that they can be further processed by computer technology and the processing result that is obtained can be output to an output device that is suitable in regard to the kind of information that it transports (for example, purely graphically visual or textual information).

In basic principle, it is conceivable in each case to record by means of optical sensors both sectional surfaces of a cut introduced in a body and correspondingly to further process the electrical data obtained from this recording in the course of the conversion to electrical signals and a subsequent digitization. This is taken into consideration above and in the patent claims by way of the formulation according to which at least one sectional surface and thus, if need be, also both sectional surfaces of a respective cut is or are optically recorded. However, this is basically unreasonable in practice, because the two sectional surfaces that are formed by a cut are largely not distinct from each other on account of the relatively small thickness of the blades used for this purpose. Nonetheless, this possibility is always included by the invention and by each of the embodiments thereof that are yet to be described, even when in part, for purposes of simplifying the description, only a sectional surface or the sectional surface of a cut is mentioned.

In accordance with the proposed method, as can be seen from the above discussions, a large-area optical recording for the invasive assessment of body properties does not occur only after a cut has been made for this purpose in the body that is to be assessed, but rather directly during a corresponding cutting operation. In regard to an application of the method in meat processing, this opens up, for example, the possibility of an assessment of meat on the basis of an optical recording of the meat directly during the meat-cutting operation, which, in final effect, advantageously leads to savings in time within the processing procedure.

In accordance with the above discussions, regardless of the respective specific case of application and the associated mechanical requirements that are placed on the cutting tool and on the size of its at least one blade, the method makes use of a specially designed blade, which makes possible the optical recording of at least one sectional surface directly during the cutting operation. Detailed discussions in this respect will be presented later in connection with the description of a system that is suitable for carrying out the method and achieving the object.

The method makes it possible, during the cutting operation conducted by means of the aforementioned blade, to visualize directly the thereby detected segments of the sectional surface on a display that is actuated as an output device by the image processing device and, in this way, to convey to persons or control personnel who are working on-site an immediate impression of the characteristics of the body in each of the segments through which the blade has passed. In accordance with a possible design of the method, it is possible, alternatively or additionally, to provide information in regard to the characteristics of the body along the cutting site, which has been optically recorded in accordance with the method, in the form of a report compiled by the image processing device after the conclusion of a cutting operation or in regard to a classification of the body. In connection with the processing of meat, it is thereby possible, in one corresponding report or in a plurality of corresponding reports, to make statements in regard to the quality grade of the meat or/and in regard to the ratio of portions of lean meat and fat. However, the corresponding situation also holds true, for example, for an application of the method in connection with the production of cheese and the quality controls that thereby take place, or also during the processing of wood and thereby, in connection with the size of the cut or solely for control purposes of cuts already made, to arrive at useful statements in regard to quality—in order to indicate at this point only once again some possibilities of application of the method in connection with the assessment of dead bodies or objects. Conceivable in connection with a possible use on a living body is, for example, the possibility that, for instance when making an incision in an abscess or in the tissue surrounding it or the like, a physician is able via the use of the method to obtain information in regard to the characteristics of the tissue in the region of the health impairment that he or she is treating directly during the cutting procedure.

In order to obtain visual or/and textual information of the above-described kind, it is not actually absolutely essential to have detailed data as to the precise position of the segment through which the blade passes in each case on the sectional surface obtained after the conclusion of the cutting operation. Thus, a statement in regard to the ratio of fat to meat that is made in the context of a report compiled during the processing of meat can be obtained in that, during image processing, the number of imaging points that are identified as fat on the sectional surface that is scanned by sensors can be placed in ratio to the number of imaging points of the scanned surface (that is, the sectional surface scanned by sensors) that are identified as meat. It is noted here that the assignment of imaging points of an image of a meat surface that is recorded by means of corresponding optical sensors or of a sectional surface produced in meat to the tissue compartments meat (muscle), fat, or bone by way of threshold value analysis of brightness values or/and color values has long been known as such to the person skilled in the art.

Whereas, as already stated, in regard to the aforementioned information compiled in reports in visual form or in textual form, a knowledge of the position of the segments that, in each case, have been optically recorded during the cutting operation can be dispensed with, if need be, this does not hold true for the visual depiction of the entire sectional surface that occurs on a display immediately after the conclusion of a cutting operation or also—to return once again to the example of meat processing—for other, yet to be mentioned below, information/statements to be taken for classification or to be conveyed in the form of reports in regard to the characteristics of meat. Therefore, in accordance with a further development of the method, by way of the image processing device, namely, by way of a position determination device that belongs to it, in assignment to the sensor signals that are obtained during the optical recording of the at least one sectional surface by the blade and the electrical data resulting from the sensor signals, positional data are transmitted to the image processing device and describe the respective momentary position of the blade within the cut body during the recording of the optical signals on which the electrical image data are based.

Taking into consideration data about the respective position of the blade, the image processing device is used after the conclusion of a cutting operation, in accordance with another possible design of the method, to create reports that make statements in regard to the total size of the sectional surface or/and in regard to characteristics of the material or tissue structure of the body on the at least one sectional surface that is produced by the cut, that is, for example, to make statements in regard to the marbling of the meat in the cut region in the case of the carcass of a slaughtered animal that is being assessed by means of the method. With a view to the preferred field of application of the invention, that is, to its use in the processing of meat, in a corresponding design of the method by the image processing device, reports are created after the conclusion of a cutting operation, these reports making statements relating to the quality grade of the meat or/and to the ratio of the proportions of lean meat and fat, but also, with respect to the latter, in regard to the positional distribution of the lean meat and fat and thus—as already addressed—in regard to the marbling. Beyond this or alternatively, the aforementioned statements in regard to the characteristics of the meat can also be utilized directly for an automated classification of the relevant part of a carcass of a slaughtered animal.

In accordance with an implementation of the method specially for the assessment of the characteristics of the meat on a beef carcass on the basis of a cut that is introduced in the region of the rib eye through the carcass of the slaughtered animal, an automated classification of the rib eye obtained when the carcass of a slaughtered animal is cut up takes place by way of the image processing device after the conclusion of a cutting operation, or/and reports are created in regard to the quality of the rib eye. Corresponding reports thereby provide statements in regard to the height, width, and area of the rib eye, namely, more specifically, statements relating to at least one but also a plurality of the aforementioned features that describe the appearance of the rib eye in the case of the assessed carcass of slaughtered beef.

In a comparable way, a design of the method that relates to the meat assessment of a slaughtered pork carcass allows statements to be made in regard to the quality of the ham or of the cutlet. A cut is made here through the pork carcass with separation of the corresponding part of the carcass of the slaughtered animal. After the conclusion of the cutting operation in the case of ham, a classification of the ham is made on the basis of the data thereby obtained, or/and reports are created, which make statements in regard to the size of the sectional surface, that is, in regard to the ham width and in regard to the ham length, or/and in regard to the distribution of the tissue compartments meat, fat, and bone, that is, in turn, in regard to one property or a plurality of properties of the ham. Likewise, it is possible in the case of a pork carcass for the image processing device, after the conclusion of the cutting operation, to carry out a classification of the cutlet for a cut made so as to separate the shoulder region and thus made through the cutlet, or/and to create reports that make statements in regard to the distribution of the tissue compartments meat, fat, and bone in the cutlet as well as in regard to the size of the sectional surface. With respect to the latter-mentioned example of the cutlet, it is also possible, for example, to cut up the complete pork loin into individual slices in a downstream processing operation, preferably by means of a so-called slicer and, in turn, immediately in the course of this process to obtain statements in regard to the characteristics and quality of the individual cutlet.

As long as at least one cut that is introduced in or through the respective body is addressed in the patent claims and in the explanations given above in regard to the method, it is self-evident to the person skilled in the art that, in the case of a cutting operation carried out by an appropriately equipped cutting tool, it is also possible to produce, at the same time, a plurality of cuts and to be able to record optically at least one sectional surface of one or a plurality of these cuts by means of optical sensors of the image acquisition unit. It is further clear to the person skilled in the art that there is also the possibility here that the image processing device further processes the electrical signals provided by the sensors of preferably a plurality of the blades after their digitization as electrical data for the purpose of a graphic visualization of the corresponding sectional surfaces for the purpose of creating reports, for the purpose of classification of the body in question, or/and for the purpose of deriving control data for downstream processes.

A suitable system for achieving the object and for carrying out the method explained above for the invasive assessment of properties of a body is composed of at least one image acquisition unit, an image processing device having at least one output device, and a cutting tool having at least one blade for making a cut in the body that is to be assessed. The image acquisition unit has optical sensors for recording optical data on at least one sectional surface of a cut made in the body with at least one blade of the cutting too, as well as (in each case) a light unit for the illumination of a respective sectional surface that is recorded by means of the sensor. The optical sensors of the image acquisition unit and the (respective) light unit for the illumination of the sectional surface that is optically recorded by means of these sensors are thereby integrated, in accordance with the invention, in at least one blade of the cutting tool. The image acquisition unit further includes units for the transmission of electrical signals or data resulting from signals of the optical sensors to the image processing device.

The aforementioned units for the transmission can involve any kind that is suitable for the transmission of electrical signals or data, in particular units for a wired transmission or for a wireless transmission. In the case that a digitization of electrical sensor signals is already produced on the part of the imaging unit, electrical data are transmitted to the image processing device in accordance with the understanding presented above. In the other case, that is, in the case of a digitization of the electrical sensor signals first in the image processing device, electrical signals are transmitted to it, whereby, in the case of a wireless transmission, preferably the former approach, that is, a digitization of the electrical signals on the part of the image acquisition unit, is provided. In accordance with the explanations just given, the image acquisition unit or the image processing device has at least one unit (more details of which are presented below) for the digitization of the electrical sensor data.

The image processing device has units for receiving the signals or data that are transmitted by the image acquisition unit. Insofar as it is provided that the image processing device receives electrical signals that have not yet been digitized from the image acquisition unit, the image processing device has, in addition, as already mentioned, a digitization unit. The image processing device is further designed to process the signals or data received from the image acquisition unit for a visualization on at least one display or/and for the creation of the reports that describe the characteristics of the body along the at least one sectional surface or/and for classification of the body or/and for the derivation of control signals.

As discussed in regard to the method, it is preferably provided in connection with the optical recording of a sectional surface, that is, of the scanning of a sectional surface, to determine within the body the respective position of the blade that optically records this sectional surface by means of its sensors. In accordance therewith, in another embodiment of the system according to the invention, the cutting tool preferably has a position determination device with position indicators, by way of which, in assignment to the sensor signals generated during the optical recording of the at least one sectional surface by the blade equipped with the optical sensors, positional data describing the respective momentary position of the blade within the body are transmitted to the image processing device.

In regard to the specific design of the optical sensors and of the light unit, different possibilities are also given. In accordance with a proposed embodiment of the system according to the invention in this respect, the optical sensors that are integrated in the at least one blade are formed by the ends of optical fibers. Furthermore, in this case—at least insofar as the site of the actual light generation is concerned—the light of a light unit that is not arranged directly in this blade is supplied directly via fiber optic cable to the sectional surface that is produced by means of the blade.

As already indicated, the system according to the invention also comprises embodiments in which the cutting tool has a plurality of blades for the simultaneous production of a plurality of cuts in the body that is to be assessed. The example of the slicer already mentioned earlier is recalled once again at this point. In this case, one or a plurality of these blades is or are equipped with optical sensors for the optical recording of at least one sectional surface of a cut introduced in the body. Insofar as, in a preferred way, a digitization of the electrical sensor signals already takes place on the part of the image acquisition unit, preferably each blade that is furnished with sensors then also has a unit for the digitization of the electrical sensor signals. However, it is also conceivable to provide a common digitization unit at a central point of the cutting tool for all blades that are equipped with sensors. A corresponding digitization unit—provided either for each blade or at a central point of the cutting tool for all blades—would thereby be formed in any case as a component part of the image acquisition unit. Likewise, in the case that electrical data are transmitted wirelessly from the image acquisition unit to the image processing device, the wireless transmission units that are required for this purpose are arranged integrally with each of the sensors or centrally at the cutting tool. In the latter case, it is possible for electrical signals or data to be transmitted from the blades, initially in a wired manner, to a corresponding central point of the cutting tool—namely, either electrical signals to a centrally arranged digitization unit or electrical data from digitization units provided integrally for each blade to centrally arranged units for wireless transmission—and then, finally, further transmitted wirelessly to the image processing device.

In conclusion, it still needs to be mentioned at this point that, in basic principle, the method can also be carried out by means of a system in which the blade or the blades of the cutting tool are operated by hand, but otherwise are equipped in accordance with the invention, that is, in which, in particular, at least one or also a plurality of the blades (not necessarily all) has or have, as integral component parts, at least optical sensors and a light unit as well as, if need be, in addition, a unit for the digitization of the sensor signals and preferably units for wireless transmission. In practice, the cutting tool has been designed in the meantime as a machine device in most cases. The system then includes, in addition, a drive device for a driving mechanism of the blade or of the blades, which is required for producing a cut in the body, as well as a control device for controlling this drive device. In this connection, it additionally needs to be noted that the blade or blades can have diverse shapes. Thus, for example, they may involve an blade-like elongated cutting edge, but also may be the cutting edge of a circular blade or slicer, which, however, is then furnished with corresponding drive means in each case.

Figure 2A:
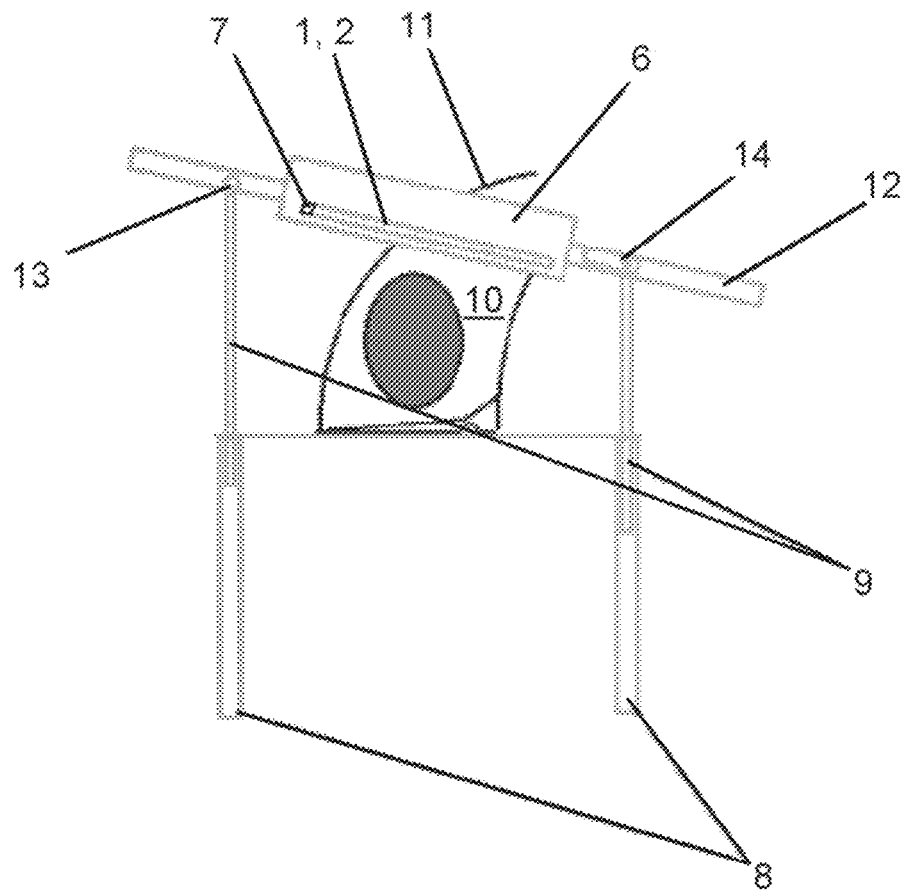
Figure 2B:
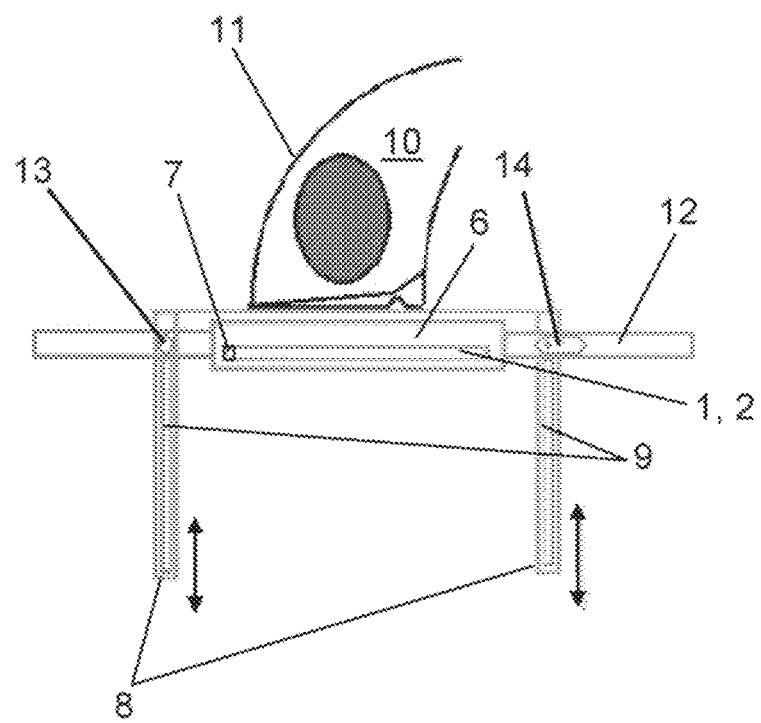

Presented in the following, on the basis of drawings, is an exemplary embodiment of the invention, which relates to the preferred application of an assessment of the meat characteristics of a carcass of a slaughtered animal in meat processing. The drawings individually show:

FIG. 1: a rough schematic illustration of a possible embodiment of the system according to the invention, FIG. 2a: details of a possible embodiment of a position determination device during the performance of a cutting operation, FIG. 2b: the position determination device in accordance with FIG. 2a after the conclusion of the cutting operation.

FIG. 1 shows a possible embodiment of the system according to the invention in a highly simplified, rough schematic illustration. The main component parts of the system are accordingly an image processing device, which is essentially composed of optical sensors 1 and a light unit 2, an image processing device 3, and a cutting tool, of which, here, only one blade 6 is shown, in which the aforementioned key elements (optical sensors 1 and light unit 2) of the image acquisition unit are integrated in accordance with the invention. Besides the elements shown in the schematic illustration here, the image acquisition unit and the image processing device 3 have units, which are not shown, for the exchange of data; namely, the image acquisition unit has at least one transmitting unit for the transmission of electrical data resulting from the signals of the optical sensors 1 and the image processing device 3 has a receiving unit for receiving the data transmitted by the transmitting unit of the image acquisition unit.

The transmission of the data between the image acquisition unit and the image processing device 3 can thereby occur, for example, in a wireless manner using a known technique for near-field communication (NFC), such as, for example, Bluetooth. In basic principle, it is obviously also conceivable to use a wired transmission, whereby the data acquired from the electrical signals of the optical sensors by way of a digitization are transported initially out of the blade 6 with its optical sensors 1 to a holding mount (not shown here) that belongs to the cutting tool (see FIG. 2a or 2b) for the blade 6 and, from it, to the image processing device 3.

In the example shown, a wireless transmission of the data resulting from the electrical signals of the sensors 1 to the image processing device is assumed. In accordance therewith, a unit 7, which is likewise indicated only schematically here, for the digitization of the sensor signals as well as a wireless transmitting unit, which is not illustrated, are integrated in the illustrated blade. In this context, the two units (the unit 7 for the digitization and the wireless transmitting unit) can be regarded as component parts of the image acquisition unit.

In the course of a cutting operation, the properties of one of the two sectional surfaces 10 (see FIG. 2a or 2b) that are formed along the cut are optically detected by means of the sensors 1. As is known, the optical sensors 1, such as, for example, a CCD array or a matrix made up of CMOS elements, involve opto-electrical converters. That is, the optical properties of the sectional surface 10 that are recorded by means of the sensors 1 are converted to corresponding electrical output signals of the sensors 1. These initially purely analog electrical signals of the sensors 1 are digitized by the unit 7, which is likewise integrated in the blade 6, as assumed in accordance with the example, and thereby converted to data, which, for further analysis—here, by way of wireless transmission—are transmitted to the image processing device 3.

By means of the image processing device 3, such as, for example, a computer workstation operating image processing software, these data are further processed for output on an output device 4, 5 that is coupled to image processing device 3. The output device 4, 5 can involve, for example, a display 4, on which the data obtained as a result of the image processing are directly visualized, so that, in each case, this display 4 graphically depicts the recorded region of the sectional surface 10 in near real time.

Also conceivable, however, it a graphic depiction of the entire sectional surface on the display 4 after the conclusion of the cutting operation or also the creation of one report or a plurality of reports by the image processing device 3, which describes or describe the properties of the sectional surface 10 and, for example, can be output to the display 4 or/and to a printer 5 in text form, whereby a corresponding report is also created by the image processing device 3 preferably only after the conclusion of the cutting operation.

An illustration of the sectional surface 10 in its entirety, which is obtained after the conclusion of the cutting operation and involves more or less a cumulative illustration of the regions of the sectional surface 10 that are recorded in succession during the cutting operation, as well as the creation of a report relating to the characteristics of the sectional surface in regard to the tissue compartments (meat, fat, and bone) or also an automated classification necessitates information as to each of the positions at which the optical properties of the sectional surface 10 are recorded by the sensors 1 of the blade 6. Therefore, a component part of the system shown in the FIG. 1 is also a position determination device 8, 9, which, however, is illustrated only symbolically in the figure.

Details of a possible embodiment of such a position determination device are shown in FIGS. 2a and 2b. However, in these drawings as well, only a possible basic principle of such a position determination device is schematically illustrated. In the example shown, the position determination device 8, 9 is formed by two guide rails 8, which, for example, are fixed in place at the feather bones and the backbone of a beef carcass 11. Guided along each of these guide rails 8 is a rod-shaped position indicator 9, one of which is hinged at a pivot point 13 of a blade holder 12 and the other of which is guided in a slot 14 of the blade holder 12 by means of a pin arranged at its end. In the course of the cutting operation, the position indicators 9 move within the guide rails 8 downward, whereby data (digitized signals) as to their depth of penetration in the guide rails 8, as recorded in a capacitive or inductive manner or by means of a change in resistance, are transmitted synchronously with the cycle of image acquisition by the sensors 1 in the blade 6 to the image processing device 3, which is not illustrated here (see FIG. 1). It is possible from these data to determine by means of conventional geometric calculations the proportions of the sectional surface with which the optical signals recorded by the sensors in the blade are associated in each case.

FIG. 2a shows the circumstances during a cutting operation. The rod-shaped position indicators 9 are inserted here in the guide rails by only a relatively short section of their total length. In FIG. 2b, the relationships after the conclusion of a cutting operation are illustrated. The rod-shaped position indicators 9 are illustrated, as in the drawing, only for clarification of the principle, with the guide rails 8 inserted over nearly their entire length, where the rod of the position indicator illustrated on the left has rotated around the hinge point (pivot point 13) with retention of its vertical orientation and the pin formed at the top end of the position indicator illustrated on the right has moved along the slot 12 from right to left.

The invention claimed is:

1. A method for the invasive assessment of properties of a body on at least one sectional surface, according to which at least one sectional surface of at least one cut introduced in this body is optically recorded by means of optical sensors of an image acquisition unit and data resulting from a digitization of the sensor signals that have been converted into electrical signals are further processed in an image processing device for at least one of the following objectives:

visualization of the at least one sectional surface on at least one display, creation of reports describing the characteristics of the body along the at least one sectional surface, classification of the body in accordance with a classification system, derivation of control signals for a subsequent further processing of the body or of parts resulting therefrom by the execution of at least one cut, is hereby characterized in that the optical recording of the at least one sectional surface is made directly during the cutting operation that creates the at least one sectional surface by way of a cutting tool blade designed for this purpose in such a way that the optical sensors of the image acquisition unit are integrated into the cutting tool blade, the optical sensors being directed at the at least one sectional surface that is made directly during the cutting operation by the cutting tool blade.

2. The method according to claim 1, further characterized in that, by way of the image acquisition unit in assignment to the sensor signals generated during the optical recording of the at least one sectional surface cut by the blade and in assignment to the electrical data resulting from the sensor signals, position data that describes the particular momentary position of the blade within the body are transmitted to the image processing device.

3. The method according to claim 1, further characterized in that the at least one cut is introduced in a carcass of a slaughtered animal or in a part of a carcass of a slaughtered animal, and the at least one sectional surface for the assessment of the meat characteristics of the carcass of a slaughtered animal or of a part thereof along this at least one sectional surface is recorded by means of the blade designed for this purpose.

4. The method according to claim 3, further characterized in that reports are created by the image processing device after the conclusion of a cutting operation, these reports making statements in regard to the quality grade of the meat or/and in regard to the ratio of the proportions of lean meat and fat.

5. The method according to claim 2, further characterized in that reports are created by the image processing device after the conclusion of a cutting operation and make statements in regard to the total size of the sectional surface or/and in regard to the marbling thereof.

6. The method according to claim 2, in application to a beef carcass for a cut made through the carcass of a slaughtered animal in the region of the rib eye, further characterized in that, after the conclusion of a cutting operation, data are determined by the image processing device in regard to at least one of the categories
height of the rib eye,
width of the rib eye,
area of the rib eye
and these data are used to make a classification of the rib eye or/and a report that describes these data is created.

7. The method according to claim 2, in application to a pork carcass for a cut made through the carcass of a slaughtered animal in order to separate the ham or the shoulder region, further characterized in that, after the conclusion of a cutting operation, data are determined by the image processing device in regard to the size of the cut piece of meat on the sectional surface, namely, in regard to the width and in regard to the length of the sectional surface, or/and in regard to the distribution of the tissue compartments of meat, fat, and bone in the cut piece of meat, and these data are used for a classification of the cut piece of meat or/and a report that describes these data is created.

8. The method according to claim 2, further characterized in that the at least one sectional surface is visualized in its entirety by the image processing device after the conclusion of a cutting operation.

9. The method according to claim 1, further characterized in that, during a cutting operation by the cutting tool, a plurality of cuts are produced at the same time and at least one sectional surface of one or a plurality of these cuts is optically recorded by means of optical sensors of the image acquisition unit.

10. A system for the invasive assessment of properties of a body on at least one sectional surface, composed of at least an image acquisition unit, of an image processing device with at least one output device, and of a cutting tool having at least one blade for making a cut in the body that creates the at least one sectional surface, wherein
the image acquisition unit has optical sensors for recording optical signals on at least one sectional surface of a cut introduced in the body with at least one blade of the cutting tool, a light unit for the illumination of the sectional surface recorded optically by means of these sensors, and units for the transmission of the sensor signals that have been converted into electrical signals or data to the image processing device,
the image processing device has units for receiving the signals or data transmitted by the image acquisition unit and is designed to process the received signals or data for at least one of the following objectives:
visualization of the at least one sectional surface on at least one display,
creation of reports describing the characteristics of the body along the at least one sectional surface,
classification of the body in accordance with a classification system,
derivation of control signals for a subsequent further processing of the body or of the parts that are created therefrom by the execution of the at least one cut
the image acquisition unit has at least one unit or the image processing device has at least one unit for the digitization of electrical signals of the optical sensors of the image acquisition unit,
further characterized in that at least the optical sensors of the image acquisition unit are integrated in the at least one blade of the cutting tool, the optical sensors being directed at the at least one sectional surface that is made directly during the cutting operation by the at least one blade of the cutting tool.

11. The system according to claim 10, further characterized in that the cutting tool has a position determination device with position indicators, by way of which, in assignment to the sensor signals resulting during the optical recording of the at least one sectional surface by the blade equipped with the optical sensors, position data describing the particular momentary position of the blade within the body are transmitted to the image processing device.

12. The system according to claim 10, further characterized in that the light unit is integrated in the at least one blade that is equipped with optical sensors.

13. The system according to claim 10, further characterized in that the at least one unit for the digitization of electrical sensor signals of these optical sensors is integrated in the at least one blade that is equipped with optical sensors.

14. The system according to claim 13, further characterized in that a wireless transmitting unit is integrated in the at least one blade of the cutting tool that is equipped with optical sensors for the transmission of data obtained by way of the digitization of the sensor signals in the at least one unit of the blade to the image processing device.

15. The system according to claim 10, further characterized in that the light of the light unit is supplied via fiber optic cable to the sectional surface produced by the at least one blade and the optical sensors integrated in this blade are formed by the ends of optical fibers.

16. The system according to claim 10, further characterized in that the cutting tool has a plurality of blades for the simultaneous production of a plurality of cuts in the body, wherein one or a plurality of these blades is or are equipped with optical sensors for the optical recording of at least one sectional surface of a cut produced by it or them in the body.

* * * * *